US008461155B2

(12) United States Patent
Wu et al.

(10) Patent No.: US 8,461,155 B2
(45) Date of Patent: *Jun. 11, 2013

(54) SCLEROSTIN AND THE INHIBITION OF WNT SIGNALING AND BONE FORMATION

(75) Inventors: Dianqing (Dan) Wu, Cheshire, CT (US); Xiaofeng Li, West Hartford, CT (US)

(73) Assignee: University of Connecticut, Farmington, CT (US)

( * ) Notice: Subject to any disclaimer, the term of this patent is extended or adjusted under 35 U.S.C. 154(b) by 309 days.

This patent is subject to a terminal disclaimer.

(21) Appl. No.: 11/084,668

(22) Filed: Mar. 18, 2005

(65) Prior Publication Data

US 2006/0030523 A1 Feb. 9, 2006
US 2012/0115787 A9 May 10, 2012

Related U.S. Application Data

(63) Continuation-in-part of application No. 10/849,067, filed on May 19, 2004.

(60) Provisional application No. 60/504,860, filed on Sep. 22, 2003.

(51) Int. Cl.
*A61K 31/535* (2006.01)
*C07C 50/18* (2006.01)

(52) U.S. Cl.
USPC .......................... 514/229.8; 552/208

(58) Field of Classification Search
None
See application file for complete search history.

(56) References Cited

U.S. PATENT DOCUMENTS

| | | | |
|---|---|---|---|
| 6,844,422 B1 | 1/2005 | Niehrs et al. | |
| 2003/0165500 A1 | 9/2003 | Rhee | |
| 2003/0181660 A1 | 9/2003 | Todd et al. | |
| 2004/0009535 A1* | 1/2004 | Brunkow et al. | 435/7.1 |
| 2004/0023356 A1 | 2/2004 | Krumlauf | |
| 2004/0038860 A1 | 2/2004 | Allen | |
| 2004/0235728 A1 | 11/2004 | Stoch | |
| 2005/0084494 A1 | 4/2005 | Prockop | |
| 2005/0196349 A1 | 9/2005 | Wu et al. | |
| 2005/0261181 A1 | 11/2005 | Wu et al. | |
| 2006/0127393 A1 | 6/2006 | Li et al. | |
| 2006/0257892 A1 | 11/2006 | Cohen et al. | |

OTHER PUBLICATIONS

DTP Datawarehouse Index Results, from http://dtp.nci.nih.gov/dtpstandard/servlet/dwindex?searchtype=NSC& outputformat=html& searchlist=366218 accessed Dec. 3, 2007.*
IIn Vivo Models, http://dtp.nci.nih.gov/docs/invivo/invivomodels.html, accessed Dec. 3, 2007, p. 33 only of 55 provided.*
NCI Communication re In Vivo screening: email From: Daniel Zaharevitz [zaharevitz@dtpax2.ncifcrf.gov], Sent: Tuesday, Dec. 4, 2007 5:37 PM, To: Gamett, Daniel C., Subject: Re: In vivo screen data, p. 1of 1.*
NCI In Vivo Screening Data http://dtp.nci.nih.gov/dtpstandard/servlet/InvivoScreen?testshortname=Tumor+PS . . . accessed Dec. 3, 2007.*
"C.I. Acid Blue 41—Compound Summary", obtained on Oct. 23, 2008 from http://pubchem.ncbi.nlm.nih.gov/summary/summary.cgi?cid=24200264&loc=ec_rcs.*
2001 NIH Consensus Conference Development Panel on Osteoporosis Prevention, Diagnosis and Therapy. JAMA 285:785-795.
Axford, John S. Glycobiology & Medicine: A Millenial Review, Jul. 11-12, 2000 lecture at 5th Jenner Symposium held at Royal Society of Medicine, London, UK, http://www/glycoscience.com/glycoscience/document_viewer.wm?FILENAME=D006.
Babij et al., 2003, J Bone Miner Res 18:960-74.
Bafico et al., 2001, Nat Cell Biol 3:683-6.
Bain et al., 2003, Biochem Biophys Res Commun 301:84-91.
Barrandon, Yann Mar. 20, 2003, Nature vol. 422:272-273.
Boyden et al., May 16, 2002, N Engl J Med 346(20):1513-21.
Capelluto et al. 2002, Nature 419(6908):726-9.
Cheyette et al. 2002, Dev Cell, vol. 2, 449-461.
Culi et al. 2003, Cell 112:343-54.
Dann et al. 2001, Nature, vol. 412, 86-90.
Erickson et al. Mar. 1973, Journal of Lipid Research, vol. 14:133-137.
Gao, Yuan et al., May 18, 2004, PNAS, vol. 101, No. 20, pp. 7618-7623.
Glinka et al, 1998, Nature 391(6665):357-62.
Glinka et al, Jun. 10, 2002, DKFZ 2001: Research Report 1999/2000: 36-40.
Gong et al. 2001, Cell 107:513-23.
Gumbiner et al. 1998, 8:430-5 Curr Opin Genet Dev.
Guo, Nini et al. Jun. 22, 2004, vol. 101, No. 25, pp. 9277-9281.
Graham et al. 2000 Cell. 103(6):885-96.
Gruneberg, et al. 2001, Angew. Chem. Int. Ed Engl. 40, 389-393.
Hey et al. 1998. Gene 216, 103-11.
Hsieh et al. 2003, Cell 112:355-67.
Hsu et al. 1998, Molecular and Cellular Biology 18:4807-4818.
Hurst 1994 J. Chem. Inf. Comput. Sci. 34, 190-196.

(Continued)

*Primary Examiner* — Daniel C Gamett
(74) *Attorney, Agent, or Firm* — Anna DiGabriele Petti, Esq.

(57) ABSTRACT

The loss of the SOST gene product sclerostin leads to sclerosteosis characterized by high bone mass (HBM). In this report, we found that sclerostin could antagonize canonical Wnt signaling in human embryonic kidney A293 cells and mouse osteoblastic MC3T3 cells. This sclerostin-mediated antagonism could be reversed by over-expression of Wnt coreceptor LRP5. In addition, we found that sclerostin bound to LRP5 as well as LRP6 and identified the first two YWTD-EGF repeat domains of LRP5 as being responsible for the binding. Although these two repeat domains are required for transducing canonical Wnt signals, canonical Wnt did not appear to compete with sclerostin for binding to LRP5. Examination of the expression of sclerostin and Wnt7b, an autocrine canonical Wnt, during primary calvarial osteoblast differentiation revealed that sclerostin is expressed at the late stages of osteoblast differentiation coinciding with the expression of osteogenic marker osteocalcin and trailing after the expression of Wnt7b. Given the plethora of evidence indicating that canonical Wnt signaling stimulates osteogenesis, we believe that the HBM phenotype associated with the loss of sclerostin may at least in part be attributed to an increase in canonical Wnt signaling resulting from the reduction in sclerostin-mediated Wnt antagonism.

2 Claims, 5 Drawing Sheets

OTHER PUBLICATIONS

Jeon et al. 2001, Nat Struct Biol 8:499-504.
Kalajzic et al. 2002, J Bone Miner Res 17(1):15-25.
Kannus et al. 2000, Osteoporos Int 11:443-8.
Kato et al. 2002, J Cell Biol 157(2):303-14.
Krupnik et al. 1999, Gene 238:301-13.
Leyns et al. 1997, Cell, vol. 88, 747-756.
Li et al. 2002, J Biol Chem 277(8):5977-81.
Li et al. 1999, EMBO J 18:4233-4240.
Li et al. 1999, J. Biol. Chem. 274:129-134.
Lilien, Ryan H. et al., Mar. 4, 2004 Dartmouth Computer Science Dept. Technical Report No. TR2004-492 at http://www.cs.dartmouth.edu/reports/reports.html.
Lips, 1997, Am J Med 103:3S-8S; discussion 8S-11S.
Little et al. 2002, Am J Hum Genet 70:11-9.
Love et al, 1995, Nature. 376(6543):791-5.
Mao et al. 2002, Nature 417:664-7.
Mao et al, Nature vol. 411:321-5.
Mao et al, 2001, Mol Cell 7:801-9.
Monaghan 1999, Mech Dev 87:45-56.
Moon RT et al, 1997, Cell, vol. 88, 725-728.
Nusse 2001, Nature 411:255-6.
Pandur et al, 2001, Bioessays 23:207-10.
Pfaffl 2001, Nucleic Acids Res May 1, 2001;29(9):e45.
Pinson et al, 2000, Nature 407:535-538.
Poy 2001, Nat Struct Biol. 8(12):1053-7.
Rarey et al, 1996 J. Mol. Biol. 261: 470-479.
Reddy, Seshamma T., et al. 2004 J Invest Dermatol 123:275-282.
Schweizer et al, 2003, BMC Cell Biol 4:4.
Semenov et al, 2001, Curr Biol 11: 951-61.
Szilagyi, Andras et al., Phys.Biol. 2 (2005) 1-16.
Takagi et al, 2003, Nature 424:969-74.
Tamai et al, 2000, Nature 407:530-5.
Tamai et al, 2004, Molecular Cell, vol. 13, 149-156.
Tolwinski et al, 2003, et al, Dev Cell 4:407-18.
Toogood, Peter L. Apr. 11, 2002, Journal of Medicinal Chemistry vol. 45, No. 8, pp. 1543-1558.
Van Wesenbeeck et al, 2003, Am J Hum Genet 72:763-71.
von Kries et al, 2000, Nat Struct Biol. 7(9):800-7.
Waszkowycz, et al, 2001, IBM Systems J. 40, 360-376.
Wang, et al, 2005 Journal of Medicinal Chemistry, vol. 48, No. 7, 2432-2444.
Wehrli, et al, 2000, Nature 407:527-30.
Wharton 2003, Dev Biol. 253(1):1-17.
Wodarz 1998, Annu. Rev. Cell Dev. Biol. 14:59-88.
Wong et al, 2003, Mol Cell. 12(5):1251-60.
Wong et al, 2000, Nat Struct Biol. 7(12):1178-84.
Xing Y et al, 2003, Genes Dev. Nov. 15, 2003;17(22):2753-64.
Wang et al., Am Chem Society, 2004.
Zuckerman 1996, N Engl J Med 334:1519-25.
Reya et al, 2005 Nature 434: 843.
Kleber et al, 2004 Curr Opin Cell Biol 16:681.
Logan et al, 2004 Annu Rev Cell Dev Biol 20: 781.
Sancho et al, 2004 Annu Rev Cell Dev Biol 20: 695-723.
Wang et al, 2004 Curr Opin Genet Dev 14: 533.
Moon et al, 2004, Nat Rev Genet 5:691.
Kawano et al, 2003, J Cell Sci 116: 2627.
Zhang et al., 2004, Mol Cell Biol 24:4677-4684.
Fujino et al., 2003, Proc Natl Acad Sci USA 100: 229.
Yamazaki et al, 2003, Biochem Biophys Res Commun 304: 229.
Hoffmann et al., 1999, J Med Chem 42: 4422.
Kramer 1999, Proteins 37: 228.
Mundy et al., 1999, Science 286: 1946.
Dunstan et al., 1999, J Bone Miner Res 14:953.
Li, et al 2001, Cell Mol Life Sci 58: 2085.
Smith, 1999, Trends Biochem Sci 24: 181.
Yuan et al, 1999, J. Biol. Chem. 274: 30419-30423.
Li et al, 2002, JBC 277; 5977-5981.
Li et al., 2005, JBC vol. 280, No. 20, 19883-19887.
Wei et al. 2006, Cell 124; 1141-1154.
Johnson et al., 2004, J Bone Disease and Mineral Research 19; 1749-1757.
Hay et al. 2005, JBC 280; 13616-13623.
Kikuchi et al., 2006, Exp Molec. Med 38; 1-10.
Semenov et al. 2005, JBC 280; 26770-26775.
Streeten et al., 2008, Bone 43(2008) 584-590.
Krane 2005, J Exp Med 201; 841-843.
Krishnan et al., 2006, J Clin Invest 116; 1202-1.
Liang et al., 2003, Cancer Cell 4:349-360.
Weeraratna et al., 2002, Cancer Cell 1:279-288.
Polakis 2000 Genes Dev 14: 1837-1851.
Behrens and Lustig 2004 Int J Dev Biol 48: 477-487.
Luu et al., 2004 Curr Cancer Drug Targets 4; 653-671.
Bafico et al., 2004 Cancer Cell 6; 497-506.
Janssens et al., 2006 Investigational New Drugs 24; 263-280.
Tian et al. 2003 NEJM 349: 2483-2494.
Oshima et al., 2005 Blood 106: 3160-3165.
Toomes et al, 2004 Am. J. Hum. Genet. 74: 751-730.
Niemann et al., 2004 Am J. Hum. Genet 74: 558-563.
Grant et al., 2006, Nature Genetics 38: 320-323.
Rodova et al., 2002 J. Biol. Chem 277: 29577-29583.
Surendran et al., Am J Physiol Renal Physiol 282: F431-F441.
Chilosi et al., 2003, Am J. Pathol. 162: 1495-1502.
Cheon et al., 2002 Proc. Nat, Acad. Sci. (USA) 99: 6973-6978.
Miyaoka et al., 1999 Schizophr. Res. 38:1-6.
Symolon et al. 2004 J. Nutr. 134: 1157-1161.
Chen H. et al. Cell 84: 491-495, 1996.
Lee G.H. Nature 379: 632-635, 1996.
Nusse and Varmus 1982, Cell 31:99-109.
Couso et al., 1995 Development 120: 621-636.
Mukhopadhyay et al., 2001 Dev Cell 1:423-434.
Li et al., 2005 Nature Genetics 37:945-952.
Mukhopadhyay et al., 2006 Development 133:2149-2154.
Pinson et al., 2000 Nature 407:535-538.
Magoori et al., 2003 J Biol Chem 278:11331-11336.
Van Amerongen and Burns, 2006 Trends Genet 12:678-389.
Bockamp et al., 2002 Physiol Genomics 11:115-132.
Raport et al., 1996 J. Biol Chem 271:17161-17166.
Deng et al., 1996 Nature 382:661-666.
Dragic et al., 1996 Nature 381-667-673.
Abrami et al., 2003 J. Cell Biol 160:321-328.
Bradley et al., 2001, Nature 414:225-229.
Scobie et al., 2003 Proc Nat Acad Sci USA 100:5170-5174.
Molloy et al., 1992 J Biol Chem 267:16396-16402.
Petosa et al., 1997 Nature 385:833-838.
Chauhan and Bhatnagar 2002, Infect Immunol 70:4477-4484.
Cunningham et al., 2002 Proc Nat Acad Sci USA 99:7049-7083.
Pannifer et al., 2001 Nature 414:229-233.
Elliot et al., 2000 Biochemistry 39:6706-6713.
Lacy et al.,2002 J. Biol. Chem. 277:3006-3010.
Rosovitz et al., 2003 J. Biol. Chem. 278:30936-30944.
Little et al., 1988 Infect Immun 56:1807-1813.
Lacy et al., 2004 Proc Nat Acad Sci USA 13147-13151.
Liu et al., Apr. 2007 Cell Microbiol 9(4):977-987.
Moayeri et al., 2006 Antimicrob Agents and Chemotherapy 50:2658-2665.
Schepetkin et al., 2006 J. Med. Chem. 49:5232-5244.
Goldman et al., 2006 BMC Pharmacology 6:8-15.
Panchal et al., 2004 Nat Struct Mol Biol 11:67-72.
Forino et al., 2005 Proc Nat Acad Sci USA 102:9499-9504.
Johnson et al., 2006 J. Med. Chem. 12:27-30.
Turk et al., 2004 Nat Struct Mol Biol 11:60-66.
Kocer et al., 2005 Infection and Immunity 73:7548-7557.
Karginov et al., 2005 Proc Nat Acad Sci USA 102:15075-15080.
Opal et al., 2005 Infect Immun 73:5101-5105.
Komiyama et al., 2005 Antimicrob Agents Chemotherapy 49:3875-3882.
Basha et al., 2006 Proc Nat Acad Sci USA 103:13509-13513.
E.L. Eliel & S.H. Wilen, Stereochemistry of Carbon Compounds, John Wiley & Sons, New York, NY, 1994, pp. 1119-1190.
Simon-Chazottes et al., 2006 Genomics 87:673-677.
Erlanson et al., 2004 J. Med Chem. 47:3463-3482.
Erlanson, 2006 Curr Opin Biotech 17:643-652.
Morrisey, 2003 Am J Path 162:1393-1397.
Pongracz and Stockley 2006 Respiratory Research 7:15.
Tickenbrock 2006 J Leuk Biol 79:1306-1311.

Figueroa et al., 2000 J. Histochem & Cytochem, 48(10):1357-1368.
Sen et al., 2000 Proc Nat Acad Sci USA 2791-2796.
Nakamura et al., 2005 Am J Path 167:97-105.
Gustafson and Smith 2006 J. Biol Chem 281:9507-9516.
Cawthorn et al., 2007 Cell Death Differ 14:1361-1373.
Diarra et al., 2007 Nature Medicine 13:156-163.
Rothbacher and Lemaire 2002 Nature Cell Biology 4:E172-E173.
Liu et al., 2003 Molec and Cell Biol 23:5825-5835.
Andl et al., 2002 Developmental Cell 2:643-653.
Sick et al., 2006 Science 1447-1450.
Papakonstantinou et al., J. Invest Dermatol 125:673-684.
Tamamura et al., 2005 J. Biol Chem. 280:19185-19195.
Hertz and Strickland, 2001 J. Clin. Invest. 108:779-784.
Zeng et al. 2008 Development 135:367-375.
Nam et al., 2006 JBC 281(19):13247-13257.
Mercurio et al., 2003 Development 131:2137-2147.
Davidson et al., Nature 438:867-872.
Swiatek et al., 2006 J. Biol Chem 281:12233-12241.
Zilberberg et al., 2004 J. Biol Chem 279:17535-17542.
Guo et al., 2006 J Med Genet 43:798-803.
Mani et al., 2007 Science 315:1278-1282.
He et al., 2005 Development 131:1663-1677.
Wu et al., 2000 Curr Biol 10:1611-1614.
Zorn, 2001, Curr Biol 11:R592-R595.
Brott and Sokol, 2002 Molec and Cell Biol 22:6100-6110.
Mikels and Nusse, 2006 PloS 4:0570-0582.
Johnson et al., 2006 Genomics 88:600-609.
Pukrop et al., 2006 Proc Natl Acad Sci USA 103:5454-5459.
Lin et al., 1994 Anal Record 240:492-506.
Miyauchi et al., 2001 Histochem Cell Biol 116:57-62.
Elbashir, S. M. et al. Duplexes of 21-nucleotide RNAs mediate RNA interference in cultured mammalian cells. *Nature* 411, 494-8 (2001).
Brummelkamp, T. R., Bernards, R. & Agami, R. A system for stable expression of short interfering RNAs in mammalian cells. *Science* 296, 550-3 (2002).
Kahler, R. A. & Westendorf, J. Lymphoid enhancer factor-1 and beta-catenin inhibit Runx2-dependent transcriptional activation of the osteocalcin promoter. *J Biol Chem* vol. 278, No. 14, 11937-44 (2003).
Mundlos, S. et al. Mutations involving the transcription factor CBFA1 cause cleidocranial dysplasia. *Cell* 89, 773-9 (1997).
Otto, F. et al. Cbfa1, a candidate gene for cleidocranial dysplasia syndrome, is essential for osteoblast differentiation and bone development. *Cell* 89, 765-71 (1997).
Komori, T. et al. Targeted disruption of Cbfa1 results in a complete lack of bone formation owing to maturational arrest of osteoblasts. *Cell* 89, 755-64 (1997).
Ducy, P., Zhang, R., Geoffroy, V., Ridall, A. 1. & Karsenty, G. Osf2/Cbfa1 : a transcriptional activator of osteoblast differentiation. *Cell* 89, 747-54 (1997).
Pandur, P., Lasche, M., Eisenberg, 1. M. & Kuhl, M. Wnt-11 activation of a non-canonical Wnt signaling pathway is required for cardiogenesis. *Nature* 418, 636-41 (2002).
Zhang, J, et al. Identification of the haematopoietic stem cell niche and control of the niche size. Nature 425, 836-841 (2003).
Itoh, K., Antipova, A., Ratcliffe, M. J. & Sokol, S. Interaction of dishevelled and Xenopus axin-related protein is required for Wnt signal transduction. *Mol Cell Biol* vol. 20, No. 6, 2228-38 (2000).
Calvi, L, et al. Osteoblastic cells regulate the haematopoietic stem cell niche. Nature 425, 841-846 (2003).
Li, Song et al., A computer screening approach to immunoglobulin superfamily atructures and interactions: Discovery of small non-peptidic CD4 inhibitors as novel immunotherapeutics, Proc Natl Acad Sci USA vol. 94, pp. 73-78, Jan. 1997.
Willert, K, et al. Wnt proteins are lipid-modified and can act as stem cell growth factors. Nature 423, 448-452 (2003).
Gregory, C, et al. The Wnt signaling inhibitor Dickkopf-1 is required for re-entry into the cell cycle of human adult stem cells from bone marrow. The Journal of Biological Chemistry 278, (30):28067-28078 (2003).
Teitelbaum, S, et al. Genetic Regulation of osteoclast development and function. Nature Genetics 4, 638-649 (2003).
Prockop, D, et al. One strategy for cell and gene therapy: Harnessing the power of adult stem cells to repair tissues. PNAS 100, Supp. 1, 11917-11923 (2003).
Brossay, L. et al. CD1d-mediated recognition of an α-galactosylceramide by natural killer T cells is hightly conserved through mammalian evolution. J. Exp. Med. 188,(8): 1521-1528 (1998).
Van der Vliet, H., et al. Potent expansion of human natural killer T cells using α-galactosylceramide (KPN7000)-loaded monocyte-derived dendritic cells, cultured in the presence of IL-7 and IL-15. J. Immunol. Methods 247, 61-72 (2001).
Taichman R.,et al. The Hematopoietic Microenvironment: Osteoblasts and the Hematopoietic Microenvironment. Hematol. 4(5):421-426 (2000).
Rattner A, et al. A family of secreted proteins contains homology to the cysteine-rich ligand-binding domain of frizzled receptors. PNAS. 94(7):2859-63. (1997).
Yamane T., et al. Wnt Signaling Regulates Hemopoiesis through Stromal Cells. J. Immunology. 167:765-772. (2001).
Johnson et al., Journal of Bone and Mineral Research, Nov. 2004, vol. 19, No. 11:1749-1757.
Gallager, 1990, Metabolism, vol. 39, issue 4, supplement 1, Apr. 1990, pp. 27-29, abstract only.
In Vivo Models, http://dtp/nci.nih.gov/docs/invivo/invivomodels.html, accessed Dec. 3, 2007, p. 33 only of 55 provided.
NCI Communication re InVivo screening: email From: Daniel Zaharevitz[zaharevitz@dtpax2.ncicrf.gov], Sent: Tuesday, Dec. 4, 2007 5:37 PM, To: Gamett, Daniel C., Subject: Re: In vivo screen data, p. 1 of 1.
NCI In Vivo Screening Data http://dtp.nci.nih.gov/dtpstandard/servlet/InvivoScreen?testshortname=tumor=PS . . . Accessed Dec. 3, 2007.
U.S. Appl. No. 09/356,294, filed Jul. 16, 1999, Rabbani et al.
U.S. Appl. No. 08/574,443, filed Dec. 15, 1995, Rabbani et al.

* cited by examiner

SCLEROSTIN AND THE INHIBITION OF WNT SIGNALING AND BONE FORMATION

REFERENCE TO RELATED PATENT APPLICATIONS

This application is a continuation-in-part of application Ser. No. 10/849,067, filed on May 19, 2004, which claims the benefit of provisional Application No. 60/504,860, filed Sep. 22, 2003. This application is also related to the patent application entitled "Compositions and Methods for the Stimulation or Enhancement of Bone Formation and the Self-Renewal of Cells," application Ser. No. 10/849,643, filed on May 19, 2004, and its contents is hereby incorporated by reference, in its entirety.

FIELD OF THE INVENTION

The present invention relates to the protein sclerostin, an antagonist and/or inhibitor of Wnt proteins. Sclerostin inhibits Wnt signaling and thus the formation of bone when it binds to the LRP5 receptor or the LRP6 receptor (LRP5/6). The invention relates to the field of therapeutic methods, compositions and uses thereof, in the treatment of bone fractures, bone disease, bone injury, bone abnormality, tumors, or growths. More particularly, the compositions and methods are directed to compounds that block sclerostin, thereby allowing bone formation to occur. The compounds were identified from a National Cancer Institute (NCI) database through various screening methods and assays. These compounds could also be modified to create derivatives or analogues not found in the NCI database or in nature which also function effectively.

All patents, patent applications, patent publications, scientific articles, and the like, cited or identified in this application are hereby incorporated by reference in their entirety in order to describe more fully the state of the art to which the invention pertains.

BACKGROUND OF THE INVENTION

The Wnt family of secretory glycoproteins is one of the major families of developmentally important signaling molecules which play important roles in embryonic induction, generation of cell polarity, and specification of cell fate. Both genetic and biochemical studies indicate that frizzled (Fz) and LRP5/6 are co-receptors for transducing canonical Wnt signaling that eventually leads to the stabilization of β-catenin and regulation of gene transcription through transcription regulators including lymphoid enhancing factor-1 (LEF-1) and T cell factors (TCF). Wnt signaling is also regulated by a number of naturally occurring antagonists that include Dickkopf (Dkk) molecules. The first Dkk (*Xenopus* Dkk-1), was initially discovered as a Wnt antagonist that plays an important role in head formation. To date, four members of Dkk have been identified in mammals. However, only the first two members (Dkk1 and Dkk2) have been well documented to function as antagonists of canonical Wnt signaling. Both Dkk1 and Dkk2 antagonize canonical Wnt signaling by simultaneously binding to LRP5/6 and a single transmembrane protein called Kremen. It has been further demonstrated that the second, but not the first, Cys-rich domains of Dkk1 and Dkk2 inhibit canonical Wnt signaling.

A myriad of evidence demonstrates that an increase in LRP5/6-mediated canonical Wnt signaling leads to an increase in bone mass. Loss-of-function mutations in LRP5 are responsible for human osteoporosis-pseudoglioma syndrome (OPPG), an autosomal recessive disorder, while putative gain of function mutations, including the Gly171 to Val substitution, are associated with human high bone mass (HBM) phenotypes. In addition, mice in which the LRP5 gene was inactivated by gene targeting showed phenotypes similar to those of OPPG patients, and the transgenic expression of $LRP5_{G171V}$ in mice resulted in HBM. Moreover, mouse primary osteoblasts showed reduced responsiveness to Wnt and low proliferation indices in the absence of LRP5, and canonical Wnts or activated β-catenin stimulated the canonical Wnt signaling activity and induced the production of an osteoblast marker alkaline phosphatase (AP) in osteoblast-like cells. The finding that inactivation of the Wnt antagonist sFRP1 enhances trabecular bone accrual further supports the idea that canonical Wnt signaling enhances bone formation. Dkk1 is expressed in differentiated osteoblast cells and osteocytes and the G171V mutation in LRP5 may cause the HBM phenotype by attenuating the antagonistic effect of Dkk1 on canonical Wnt signaling.

Itasaki et al. described a new Wnt antagonist called WISE. WISE appears to be a context-dependent regulator of Wnt signaling; it may inhibit or stimulate Wnt signaling in different assays in *Xenopus*. WISE was also shown to bind to LRP6 and compete with Wnt8 for binding to LRP6. WISE shares 38% amino acid identity with sclerostin, the gene product of SOST. Loss of function mutations of SOST are responsible for an autosomal recessive sclerostin skeletal disorder. Previous studies have shown that sclerostin was highly expressed in osteocytes and that it might act as a bone morphogenetic protein (BMP) antagonist, but another study suggested that sclerostin might not be a functional BMP antagonist and speculated that it might modulate Wnt signaling. In this report, we now clearly demonstrate that sclerostin can bind to both LRP5 and LRP6 and act as a Wnt antagonist. Because sclerostin expression occurs after peak Wnt7b expression during the osteogenic differentiation, the reduction in sclerostin-mediated antagonism of Wnt signaling contributes to the increases in bone mass associated with SOST.

SUMMARY OF THE INVENTION

The present invention is directed to methods and compositions that address several problems related to bone remodeling, such as osteoporosis and other bone diseases. The invention also provides for the use of compositions to aid in the healing of fractures or other injuries or abnormalities of bone. In particular, the invention provides a process for promoting bone formation in a mammalian subject comprising administering to the subject an effective amount of compounds which prevent the binding of sclerostin.

The invention further provides for gene therapy methodologies for clinical conditions characterized by insufficient bone formation comprising administering an effective amount of a compound that prevents sclerostin binding, or by causing a decrease in the expression of sclerostin.

In other aspects of the invention, gene expression, detection and quantification of sclerostin or related proteins serve as potential diagnostic methods for a variety of bone diseases.

The present invention is also directed to methods and compositions that address tumors or other bone growths.

The present invention has identified compounds which, when provided to a cell, bind to, interact with, or fit into sites or cavities found on the domains of the co-receptors involved in the stimulation, enhancement, inhibition or regulation of bone formation, or bone remodeling. These receptors include the LRP5 receptor, the LRP6 receptor, the frizzled receptor or any other receptor involved in the LRP5 or LRP6 (LRP5/6) receptor system.

The compounds were identified using screening methods described in patent application Ser. No. 10/849,067. These compounds were found to disrupt the sclerostin and LRP5/6 interaction. Other compounds inhibited Wnt signaling by inhibiting the binding of Wnt to LRP5/6. The compounds of the present invention are non-native, or exogenous compounds which are not present in the cell, but originate from an outside source. Specifically, the compounds identified as IIIC3 ($NCI_{8642}$) and IIC8 ($NCI_{366218}$) were found to disrupt the sclerostin and LRP5/6 interaction. As shown on FIG. 5, the binding of sclerostin-AP (a fusion protein of sclerostin and alkaline phosphatase) to LRP5 decreased when either 111C3 or 11C8 was added. The compounds bind to LRP5/6, and therefore prevent sclerostin from binding, blocking Wnt and probably inhibiting bone formation.

DETAILED DESCRIPTION OF THE INVENTION

Because of the homology shared between WISE and sclerostin, experiments were carried out to determine whether sclerostin would exert an effect on canonical Wnt signaling. The effect of conditioned medium (CM) containing mouse sclerostin on Wnt3a-induced activation of canonical Wnt signaling was determined using the LEF-1-based reporter gene assay in human embryonic kidney (HEK) cells. Sclerostin-containing CM showed marked inhibition of Wnt3a activity in a dose-dependent manner (FIG. 1A). Because control CM started to show significant inhibition at 50 micro-liters, higher doses were not tested. To further confirm this effect of sclerostin, sclerostin and another canonical Wnt, Wnt1, were coexpressed in HEK cells, and sclerostin showed up to 60% inhibition of the activity of coexpressed Wnt-1 (FIG. 1B, bars 2&4). Interestingly, coexpression of LRP5 abolished the antagonistic effect of sclerostin on Wnt signaling, and a slight stimulation of Wnt1 signaling by sclerostin was even observed in the presence of coexpressed LRP5 (FIG. 1B, bars 6&8). The effect of sclerostin on Wnt signaling in an osteoblastic cell line MC3T3 was also examined. Expression of sclerostin also showed up to 70% inhibition of Wnt-1 activated reporter gene activity in MC3T3 cells (FIG. 1C, bars 2&4). Once again, expression of LRP5 reversed the inhibition (FIG. 1C, bars 6&8). However, there was no increase in Wnt1 activity in MC3T3 cells when sclerostin and LRP5 were expressed with Wnt (FIG. 1C). Nevertheless, all these results clearly demonstrate that sclerostin antagonizes canonical Wnt activity activated by canonical Wnts when LRP5 is expressed at endogenous levels.

To understand how sclerostin antagonizes canonical signaling, experiments were carried out to determine if sclerostin binds to LRP5/6 directly. The binding of sclerostin-alkaline phosphatase (AP) fusion protein to cells expressing exogenous LRP5 or LRP6 were measured, with the same methods used for Dkk1-AP. As shown in FIG. 2A, sclerostin-AP showed a LRP6-binding curve similar to Dkk1-AP, suggesting that sclerostin-AP has an affinity for LRP6 comparable to that of Dkk1-AP, which was previously determined to be sub-nanomolar. The binding of sclerostin-AP and Dkk1-AP to LRP5-expressing cells revealed that sclerostin. -AP and Dkk1-AP also have similar affinities for LRP5 (FIG. 2B). To delineate which regions of LRP5 are responsible for the binding of sclerostin-AP, we measured the binding of sclerostin-AP to two LRP5 mutants that lack either the first or last two YWTD-EGF repeat domains. These mutants are designated as LRP5R12 or LRP5R34, respectively (FIG. 2E). While Dkk1-AP was capable of binding to both LRP5 mutants (FIG. 2D), sclerostin-AP could only bind to LRP5R12, but not LRP5R34 (FIG. 2C).

We have previously shown that LRP5R12 was still able to transduce Wnt signaling, suggesting that this LRP5 mutant may still retain the Wnt-binding sequences. To determine if sclerostin and Wnt compete with each other for the binding to LRP5R12, the binding of sclerostin-AP to cells expressing LRP5R12 in the presence or absence of Wnt3a CM was measured. The presence of Wnt3a did not affect the binding of sclerostin-AP to LRP5R12 at all (FIG. 3A). In contrast, the presence of Dkk1 completely blocked the binding of sclerostin-AP to LRP5R12 (FIG. 3B). In an attempt to further delineate sclerostin binding sequences on LRP5, two additional LRP5 mutants were constructed, which lack the second to fourth YWTD-EGF repeat domains and the first, third, and fourth YWTD-EGF repeat domains, respectively. However, these two LRP5 mutants did not bind to either sclerostin-AP or Dkk1-AP, nor did they transduce Wnt signaling. These results suggest that, either both first and second YWTD-EGF repeat domains are required for the binding of sclerostin to LRP5 or these LRP5 mutants were incorrectly folded.

Several LRP5 mutations in the first YWTD-EGF repeat domain have been found to be associated with HBM. We have previously characterized one of the mutations, G171V, and found that this mutation interfered with the interaction of LRP5 with its chaperon Mesd, resulting in poor transportation of LRP5 to cell surfaces. Because this LRP5 mutant was still able to transduce signals intracellularly for autocrine Wnts, it was thought that the mutation may increase Wnt signaling by retaining the LRP5 receptor inside the cells from extracellular antagonists such as Dkk1 because Dkk1 is highly expressed in osteocytes. The finding of sclerostin as a new Wnt antagonist, which is known to be expressed in the bone and osteocytes, may provide alternative explanations for the effects of the G171V mutation, which is located in the first YWTD-EGF repeat domain and within the sclerostin-binding region. One of such explanations may be that the G171V mutation directly interferes with the binding of LRP5 to sclerostin. To test this possibility, we measured and compared the binding of sclerostin-AP to LRP5G171V with that of Dkk1-AP. As we have previously shown, cells expressing LRP5GV have a five-fold lower apparent binding to Dkk1-AP than cells expressing wildtype LRP5 (FIG. 3C) due to the interference of the chaperon's function by the mutation. Similarly, cells expressing LRP5GV also showed a reduction in the binding of sclerostin-AP to the same degree (FIG. 3B). As the G171V mutation does not directly interfere with the interaction between LRP5 and Dkk1, it is also unlikely that the mutation interferes with the interaction between LRP5 and sclerostin. The observation that LRP5GV could still reverse sclerostin-mediated inhibition of Wnt activity in the same dose range as the wildtype LRP5 (FIG. 1B,C) provides further support for the idea that the G171V mutation does not interfere with the interaction between LRP5, or LRP6 and Dkk1.

Sclerostin has been previously shown to be primarily expressed in osteocytes. We examined sclerostin expression in relation to Wnt7B expression during primary calvarial osteoblast differentiation. We previously identified Wnt7b, a canonical Wnt that can stabilize β-catenin, as the only Wnt that showed drastic changes in its expression levels during primary bone marrow osteoblast differentiation. Similarly, the expression levels of Wnt7b showed drastic changes during calvarial osteoblast differentiation; the expression of Wnt7b peaks at Day 8 and then receded to lower levels, preceding the expression of osteogenic marker osteocalcin and another Wnt antagonist Dkk1 (FIG. 4A). In situ hybridization further confirms the conclusion on Wnt 7b expression in that Wnt7b mRNA was detected primarily in early undifferentiated osteoblasts in a mouse long bone (FIG. 4B). The expression of sclerostin showed a similar time course to that of osteocalcin and only occurred at the late stages of the differentiation when presumably osteocytes are forming in the mineralized matrix (FIG. 4A). This pattern of sclerostin expression is consistent with previous in vivo observations that sclerostin is expressed in osteocytes buried in the bone matrix and may play a role in mechanical loading. On the basis of the expression patterns of sclerostin and Wnt7b, we postulate that sclerostin contributes to the G171V-associated HBM phenotype even though sclerostin may not directly interfere with Wnt binding or the mutation does not affect sclerostin binding to LRP5. As suggested by our hypothesis that the G171V mutation may hide the receptor from paracrine antagonists without diminishing the signaling ability of the mutant receptor for autocrine Wnt, sclerostin, which is only produced by well differentiated osteoblasts or osteocytes, would be one of such paracrine antagonists that conceivably has less access to LRP5G171V than the wildtype LRP5. Thus, the G171V mutation may increase Wnt activity by attenuating the antagonism of canonical Wnt signaling by not only Dkk1, but also sclerostin and potentially other paracrine Wnt antagonists present in the bone.

In previous studies, sclerostin was shown to act as a BMP antagonist. It is convincing that sclerostin has a reasonably high affinity for BMP6 and BMP7. However, the biological effects of sclerostin on BMP was merely determined by measuring BMP-induced alkaline phosphatase (AP) activity 3-6 days post ligand addition in osteoblastic cells. This AP activity readout is not specific for BMP activity. In fact, canonical Wnts can also stimulate AP activity in these types of cells. In contrast, our Wnt reporter gene assay is specific for canonical Wnt and cannot be activated by BMP in HEK cells (data not shown). In addition, in the assay using CM, we measured the effect of sclerostin in 6 hours (FIG. 1A). Given the recent observations that sclerostin failed to inhibit early responses elicited by BMP, we believe that it is more likely that sclerostin is biologically a canonical Wnt antagonist and that its effects on bone mass is probably primarily attributed to its antagonistic effect on canonical Wnt signaling.

As shown in FIG. 2, sclerostin binds to the first two YWTD-EGF repeat domains of LRP5, which are also required for transducing Wnt signals. However, our evidence suggests that the antagonistic effect of sclerostin is unlikely due to direct competition with Wnt for LRP binding, because 1) Wnt3a failed to inhibit the binding of sclerostin-AP to LRP5; and 2) LRP5 could reverse the inhibitory effect of sclerostin on canonical Wnt signaling. The latter observation is reminiscent of the effect of Dkk1 on Wnt signaling as Dkk1 suppression of Wnt signaling can also be reversed by exogenous expression of LRP5/6. The reason for the ability of LRP5/6 molecules to reverse Dkk's effects is because Dkk-mediated antagonism requires another protein Kremen. When Kremen is coexpressed with LRP5/6, Dkk-mediated inhibition could be restored. Although Kremen had no effect on sclerostin-mediated antagonism, we suspect that a similar mechanism may be used by sclerostin to inhibit Wnt signaling. In other words, there may be accessory proteins like Kremen that may be required for sclerostin to function efficiently as an antagonist. Recently, noggin has been shown to directly interact with sclerostin and inhibit noggin's capacity to inhibit BMP signaling. Thus, noggin, once bound to sclerostin, might inhibit sclerostin capacity to modulate Wnt signaling. In addition, the observation that sclerostin showed slight stimulation of the LEF-1 reporter gene activity in the presence of exogenous LRP5 or LRP5GV suggests that sclerostin may be a partial agonist under certain circumstances, even in mammalian systems.

The present invention provides methods for promoting or regulating bone formation or bone remodeling comprising administering at least one non-native compound, a fragment of a non-native compound, or any combination thereof. A non-native compound is defined as a compound that is not naturally found in a mammalian subject, a human body in particular. A non-native compound may also comprise an artificially manufactured compound that is identical to a compound that is naturally found in the human body. When the non-native compound or compounds bind to a receptor or co-receptor involved in bone formation or bone remodeling, the binding of sclerostin is prevented, thereby allowing bone to form.

Two or more non-native compounds may join together directly through cross-linking, for example, or indirectly through a linker arm. Each of these linked compounds may dock in different locations on the same binding site, protein or receptor. Each of these linked compounds may also dock in different locations on different binding sites, proteins or receptors.

The compounds or fragments of compounds may be a small molecule, protein, peptide, polypeptide, cyclic molecule, heterocyclic organic molecule, nucleic acid, lipid, charged lipid, polar lipid, non-polar lipid, sugar, glycoprotein, glycolipid, lipoprotein or chemical. The compounds or fragments may also be agonists, antagonists, partial agonists, or any combination of the aforesaid.

The compound may be administered by inhalation, orally, intravenously, intraperitoneally, intramuscularly, parenterally, transdermally, intravaginally, intranasally, mucosally, sublingually, topically, rectally or subcutaneously.

The present invention also provides a method for identifying a compound or drug candidate that will bind to a signal peptide or protein involved in protein-protein interactions, to inhibit or promote the occurrence of subsequent events. Specifically, the compound or drug candidate will bind to the receptor protein to inhibit or promote bone formation or bone remodeling. The first step involves determining the virtual or computational structure of the receptor protein through the use of various methods such as amino acid sequencing, X-ray crystallography, NMR, analogs or derivatives of the receptor protein, or any combination of the aforesaid methods. In a preferred embodiment, the protein is non-soluble or membrane-bound.

The next step involves identifying a particular binding cavity site or domain on the receptor protein through the use of experiments based on biological function comprising mutational analysis, chemical modifications (of amino acids, for example), co-crystallography, NMR or any combination of the aforesaid methods. Using the results obtained from these experiments, such as mutations and chemical modifications, a specific binding site or domain is identified within the binding cavity to which the compound or drug candidate will bind. The entire binding cavity or a specific binding site within the cavity may be used to screen for a compound that fits and binds. The screening is conducted using the UNITY™ program. The docking of the compound into the cavity is carried out through the use of the Flexx™ program. The compound with the highest binding affinity or the lowest binding energy using the Cscore™ program is then selected. The ultimate goal is to select a compound or drug candidate with the best fit.

A preferred embodiment of the invention is a method for preventing or blocking bone formation in a mammalian subject by administering sclerostin.

Another preferred embodiment of the present invention is a method for the treatment of abnormal bone growth comprising administering an antibody for sclerostin, or any other compound or fragment of a compound which decreases or eliminates sclerostin, or decreases or eliminates the affinity of sclerostin to a receptor or co-receptor involved in bone formation or bone remodeling.

MATERIALS AND METHODS

Cell Culture, Transfection, Preparation of CM, and Luciferase Assay.

Human embryonic kidney cell (HEK) line A293T and mouse osteoblastic cell line MC3T3 were maintained and transfected as previously described. For luciferase assays, cells in 24-well plates were seeded at $5 \times 10^4$ cells/well and transfected with 0.5 µg DNA/well using Lipofectamine Plus (Invitrogen, CA), as suggested by the manufacturer. The LacZ plasmid was usually used to make DNA concentrations equal for each transfection. Cell extracts were collected 24 hr after transfection. Luciferase assays were performed as previously described. Luminescence intensity was normalized against fluorescence intensity of GFP. For preparation of DKK1-AP and sclerostin-AP containing CM, HEK cells were seeded in 6 well-plates at $4 \times 10^5$ cells/well and transfected with 1 µg DNA/well. CMs were collected 48 hr after transfection.

Construction of Expression Plasmids and Mutagenesis.

The wild-type and mutant forms of human LRP5, LRP6, mouse Wnt1, DKK1, sclerostin, and DKK-2 were generated by PCR using the high fidelity thermostable DNA polymerase Pfu Ultra (Stratagene, Calif.). nucleotide sequences were verified by DNA sequencing. HA or Flag epitope tags were introduced to the C-termini of the full-length and mutant molecules. The expression of these molecules was driven by a CMV promoter. The LEF-1 reporter gene constructs were kindly provided by Dr. Grosschedl.

DKK1-AP and Sclerostin-AP Binding Assay.

HEK cells in 24-well plates were transfected with LRP5 and its mutants. One day later, cells were washed with cold washing buffer (HBBS containing BSA and $NaN_3$) and incubated with mouse DKK1-AP or sclerostin-AP CM on ice for two hours. Then, cells were washed three times with the washing buffer and lysed. The lysates were heated at 65° C. for 10 min, and its AP activity was determined using a Tropix luminescence AP assay kit. The immunoprecipitation assays were carried out essentially as previously described.

Primary Calvarial Osteoblast Culture.

Mouse calvarial osteoblast cultures from 5 day old mice were generated as previously described and were induced to undergo osteogenic differentiation in the presence of 8 mM β-Glycerophosphate, and 50 ug/ml ascorbic acid. Media were changed every two days.

Quantitative PCR Analysis.

Total RNA was isolated using the TRIzol reagent (Invitrogen) according to manufacturer's instructions. For QPCR analysis, RNA was reverse-transcribed by SuperScript™ First-Strand Synthesis System for RT-PCR (Invitrogen). QPCR was carried out using QuantiTect™ SYBR Green PCR kit (Qiagen) on a DNA Engine OPTICON™ (MJ Research Inc.) instrument. B-actin was used as an internal reference for each sample. Using a formula previously described, the relative change in mRNA levels was normalized against the β-actin mRNA levels.

In situ Hybridization.

The full-length coding region of Wnt7b was used to synthesize anti-sense and sense probes. The probes were labeled with Digoxigenin using an RNA Labeling Kit (Roche, Indianapolis, Ind., USA). Sections of the tibia from a 3-weeks old mouse were dewaxed, rehydrated and fixed again with 4% paraformaldehyde. Then the section s were treated with 2% glycine and Proteinase-K and acetylated using an acetic anhydride/TEA solution, followed by hybridization with a digoxygenin-labelled probe. After washing the sections with 50% formamide, 5×SSC, 5% SDS for 30 minutes at 70° C. twice and 50% formamide, 2×SSC for 30 minutes at 65° C., the sections were incubated with anti-digoxigenin-alkaline phosphatase antibody followed by Nitro Blue etrazolium/4-bromo-5-chloro indolylphosphate, which yields a purple blue color. The sections were also counterstained with methyl green (nuclei) and orange G (cytoplasma).

A) Effects of sclerostin CM on Wnt3a CM. Wnt3a CM (25 ul) were mixed with varying amounts of Sclerostin CM (SCM) or control CM (CCM) and added to HEK cells transfected with the LEF-1 reporter gene. Six hours later, cells were lysed, and luciferase activity was determined. The activity in the absence of SCM is taken as 100%. Wnt3a CM increased reporter gene activity by 5 folds. Expression of Flag tagged sclerostin was detected by an anti-Flag antibody (insert). B,C) Effects of coexpressed sclerostin on Wnt1 signaling in HEK (B) and MC3T3 (C) cells. Cells were transfected with cDNAs encoding Wnt1, Sclerostin (Scl), wildtype LRP5 (Wt), or G171V LRP5 (GV) as indicated in the figure and the LEF-1 reporter gene and a GFP expression plasmid. One day later, cells were lysed, and the GFP levels and luciferase activities were determined and normalized against GFP levels.

Figure 1:
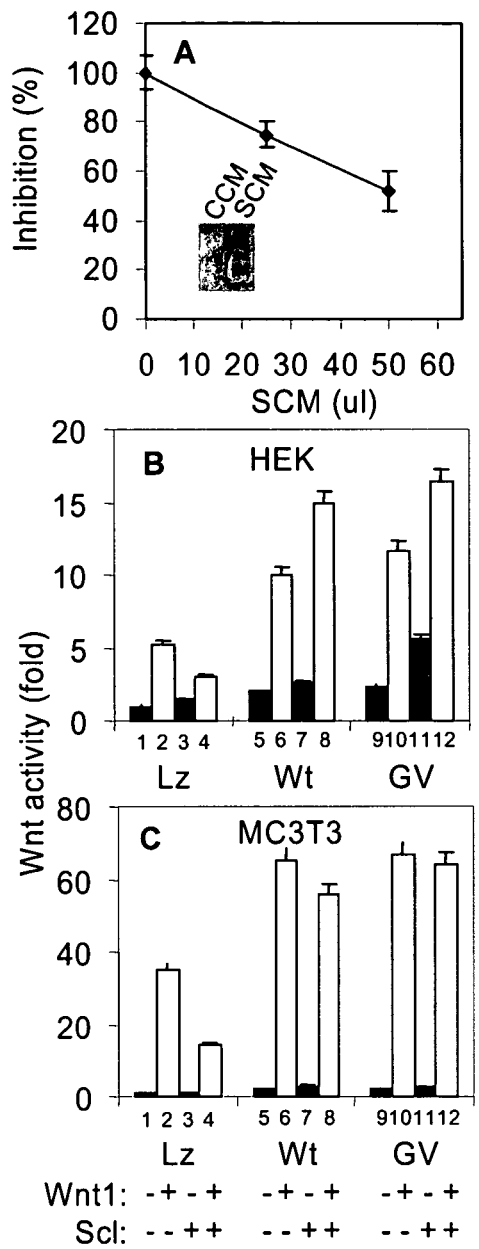
FIG. 1. Sclerostin antagonizes canonical Wnt signaling.
Figure 2:
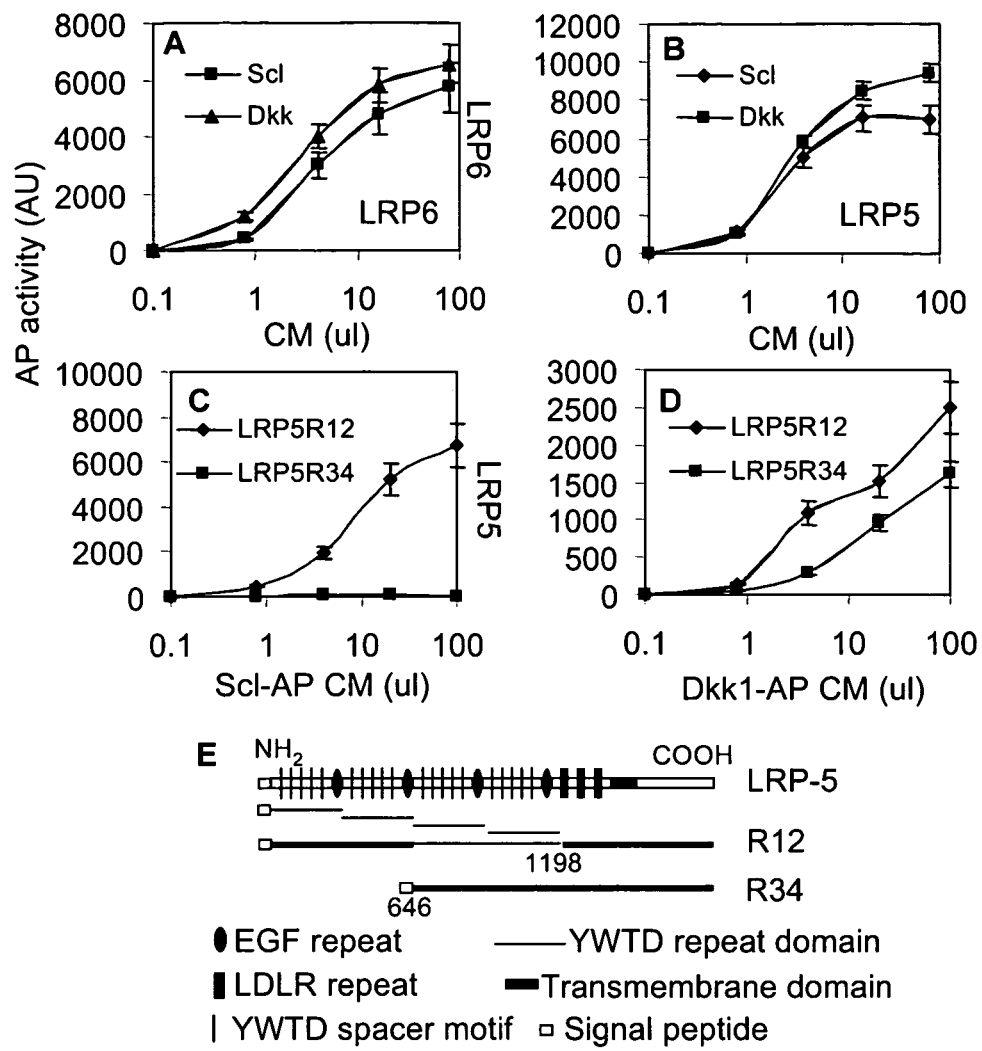

FIG. 2. Binding of sclerostin-AP to LRP5 and its mutants.

A,B) Binding of Dkk1-AP and sclerostin-AP to full length LRP5, LRP6 or LacZ. HEK cells were transfected with the full-length LRP6 (A) or LRP5 (B). Binding of Dkk1-AP or sclerostin-AP (Scl) was determined as described in the Method. Binding to cells transfected with control plasmid LacZ was subtracted as non-specific binding. Specific binding is presented in the charts. B,C) Binding of Dkk1-AP and sclerostin-AP to LRP5 mutants. HEK cells were transfected with LacZ or LRP5 mutants as indicated. Binding of sclerostin-AP (C) and Dkk1-AP (D) was determined. (E) Schematic representation of LRP5 mutants.

Figure 3:
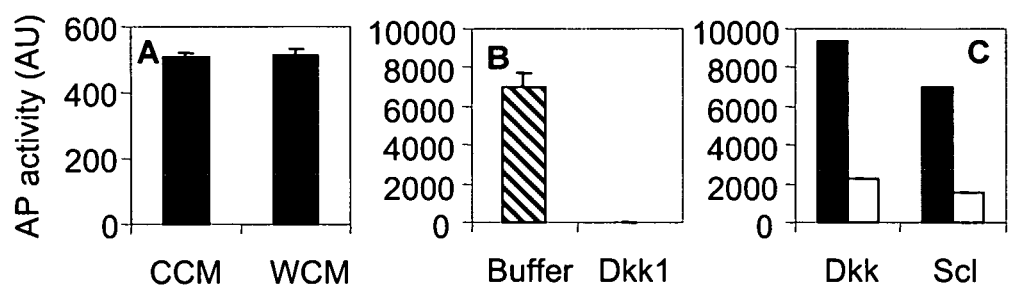

FIG. 3. Effects of Wnt3a, Dkk1, and LRP5 mutation on sclerostin binding.

A) HEK cells were transfected with LRP5. Binding of sclerostin-AP (5 ul) was determined in the presence of control CM (CCM) or Wnt3a CM (WCM, 100 ul). B) HEK cells were transfected with LRP5R12. Binding of sclerostin-AP (50 ul) was determined in the presence of buffer or recombinant Dkk1 (10 nM). C) HEK cells were transfected with LRP5 (black bars) or LRP5G171V (white bars). Binding of Dkk1-AP (Dkk) or Sclerostin-AP (Scl) was determined. In all these binding assays, binding to cells transfected with control plasmid LacZ was subtracted as non-specific binding. Specific binding is presented in the charts.

Figure 4:
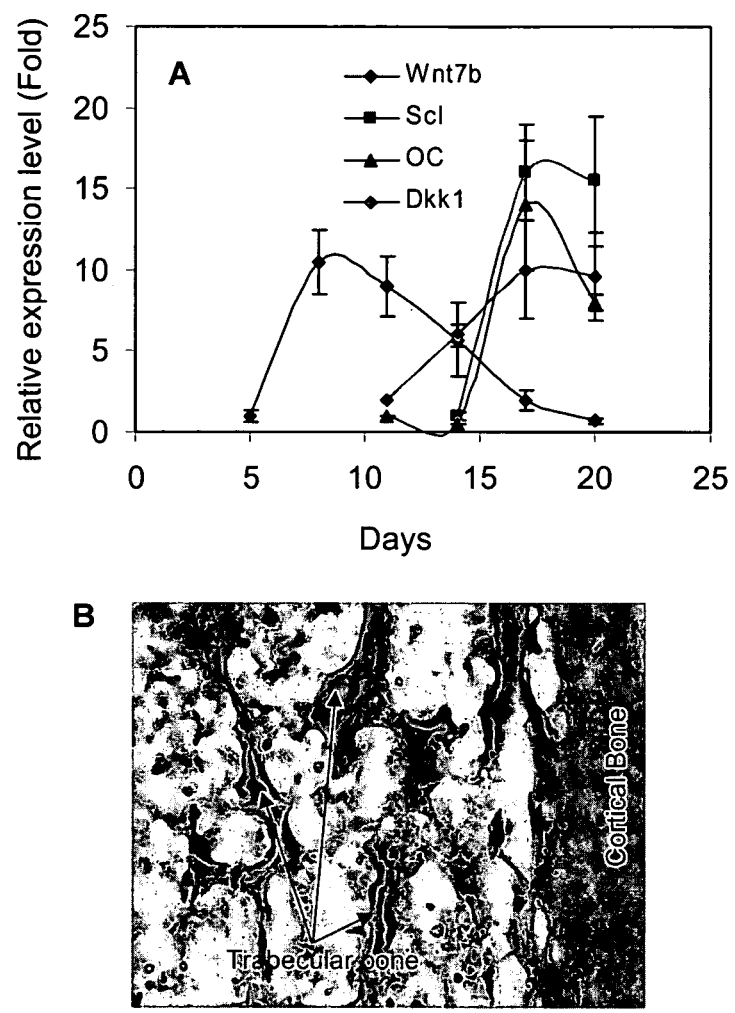

FIG. 4. Expression of Wnt7b, sclerostin, Dkk1, and osteocalcin.

A) Primary calvarial osteoblast cultures were established from 5 days old mice. Differentiation inducers were added on day 5. Relative expression levels of Wnt7b, sclerostin (scl), osteocalcin (OC), and Dkk1 were determined by QRT-PCR as described in the Methods. B) Expression of Wnt7b in a mouse long was examined using in situ hybridization. Wnt7b (dark stain) is primary detected in osteoblasts. Nuclei are counterstained in green.

Figure 5:
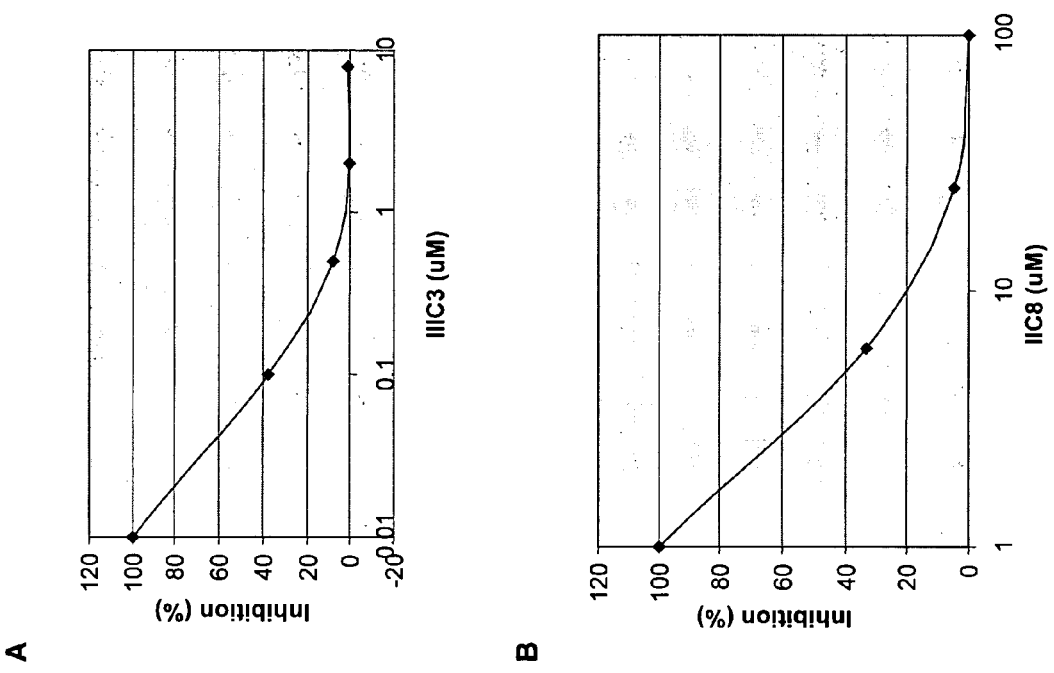

FIG. 5. Effect of IIIC3 and IIC8 on the binding of sclerostin-AP to LRP5.

A) The inhibition of bone formation was inversely related to the amount of IIIC3 present. The greater the amount of IIIC3 added, the lower the percentage of the inhibition of bone formation. B) The greater the amount of IIC8 added, the lower the percentage of the inhibition of bone formation.

The invention claimed is:

1. A method for promoting bone formation or bone remodeling in a subject having a need thereof, the method comprising administering at least one compound, wherein said compound binds to a YWTD domain of an LRP5 or LRP6 receptor thereby disrupting the interaction of sclerostin with the LRP5 or LRP6 receptor and promoting bone formation or bone remodeling, wherein said compound comprises

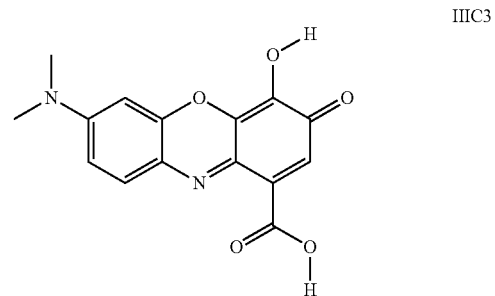 [SMILES: CN(C)c1ccc2nc3c(C(=O)O)cc(=O)c(O)c-3oc2c1]

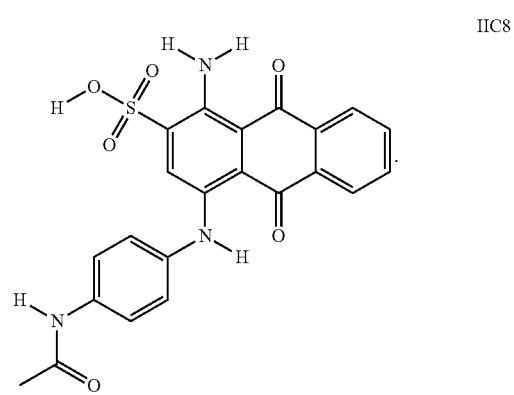 [SMILES: CC(=O)Nc1ccc(Nc2cc(S(=O)(=O)O)c(N)c3c2C(=O)c2ccccc2C3=O)cc1]

or

2. The method of claim 1, wherein said compound consists of IIIC3 or IIC8.

* * * * *